US007297552B2

(12) United States Patent
Kobayashi

(10) Patent No.: US 7,297,552 B2
(45) Date of Patent: Nov. 20, 2007

(54) INSTRUMENTS FOR FORMING AN IMMOBILIZED SAMPLE ON A POROUS MEMBRANE, AND METHODS FOR QUANTIFYING TARGET SUBSTANCES IN IMMOBILIZED SAMPLES

(75) Inventor: Hironori Kobayashi, Ono (JP)

(73) Assignee: Sysmex Corporation, Kobe-shi (JP)

( * ) Notice: Subject to any disclaimer, the term of this patent is extended or adjusted under 35 U.S.C. 154(b) by 393 days.

(21) Appl. No.: 10/821,471

(22) Filed: Apr. 8, 2004

(65) Prior Publication Data

US 2005/0226784 A1 Oct. 13, 2005

(51) Int. Cl.
*G01N 33/558* (2006.01)

(52) U.S. Cl. ...................................................... 436/514

(58) Field of Classification Search ................ 436/514, 436/517, 518; 435/4, 7.1, 7.91, 287.1, 287.2, 435/287.8, 287.9, 288.2–288.6; 422/58
See application file for complete search history.

(56) References Cited

U.S. PATENT DOCUMENTS 4,493,815 A * 1/1985 Fernwood et al. .......... 422/101
4,833,087 A * 5/1989 Hinckley ..................... 422/58
6,168,914 B1 * 1/2001 Campbell et al. .............. 435/4

FOREIGN PATENT DOCUMENTS

JP 01-223352 9/1989
JP 2000-329766 11/2000

* cited by examiner

*Primary Examiner*—Ann Yen Lam
(74) *Attorney, Agent, or Firm*—Brinks Hofer Gilson & Lione

(57) ABSTRACT

Instruments for forming an immobilized sample on a porous membrane are described, a representative one of which includes: (a) a first plate containing a first connector and a first region provided with a plurality of through-holes; and (b) a second plate containing a second connector configured for engaging the first connector and a second region provided with a plurality of through-holes. A porous membrane is interposed between the first region and the second region by engagement of the first connector and the second connector. Methods for quantifying a target substance in an immobilized sample are also described.

17 Claims, 14 Drawing Sheets

| Specimen No. | Net Fluorescent Intensity [CNT/mm$^2$] | Calibration Curve Conversion Amount [U/mL] |
|---|---|---|
| 1 | 36.5 | 30.5 |
| 2 | 42.9 | 35.8 |
| 3 | 13.2 | N.D |
| 4 | 43.1 | 36.0 |
| 5 | 36.2 | 30.2 |
| 6 | 73.0 | 60.9 |
| 7 | 20.9 | N.D |
| 8 | 81.1 | 67.8 |
| 9 | 31.2 | 26.1 |
| 10 | 57.0 | 47.6 |
| HL60 | 239.7 | 200.1 |
| Jurkat | 627.1 | 523.7 |

INSTRUMENTS FOR FORMING AN IMMOBILIZED SAMPLE ON A POROUS MEMBRANE, AND METHODS FOR QUANTIFYING TARGET SUBSTANCES IN IMMOBILIZED SAMPLES

FIELD OF THE INVENTION

The present invention relates to instruments for forming an immobilized sample on a porous membrane, and to methods for quantification of a target substance in an immobilized sample using the instrument.

BACKGROUND

Clinical specimens and excised samples of diseased tissues may contain various types of proteins. Enzyme-linked immunosorbent assay (ELISA) is a typical method for detecting specific proteins present in minute quantities in such samples.

The immunoconcentration method is known as a fast and simple ELISA method. This method titrates a specimen on a porous film (membrane) on the surface of which an immobilized antibody has been fixed beforehand to produce an antigen-antibody reaction on the membrane. A detection reagent is titrated onto the membrane to produce a color reaction, and then a wash solution is titrated to clarify the color (for example, see: Japanese Laid-Open Patent Nos. H1-223352 and 2000-329766).

When a plurality of items are to be assayed, the preparation of the porous membrane on which an antibody has been previously fixed requires that a number of types of porous membranes or solid-phase plates corresponding to the number of items to be assayed are prepared, thereby reducing assay efficiency.

SUMMARY

The scope of the present invention is defined solely by the appended claims, and is not affected to any degree by the statements within this summary.

A first instrument for forming an immobilized sample on a porous membrane embodying features of the present invention includes: (a) a first plate containing a first connector and a first region provided with a plurality of through-holes; and (b) a second plate containing a second connector configured for engaging the first connector and a second region provided with a plurality of through-holes. A porous membrane is interposed between the first region and the second region by engagement of the first connector and the second connector.

A second instrument for forming an immobilized sample on a porous membrane embodying features of the present invention includes: (a) a first plate containing a first region provided with a plurality of through-holes; and (b) a second plate containing a connector configured for engaging the first plate, which contains a second region provided with a plurality of through-holes. A porous membrane is interposed between the first region and the second region by engagement of the connector and the first plate.

A method for quantifying a target substance in an immobilized sample embodying features of the present invention includes: (a) providing an instrument comprising a first plate, the first plate comprising a first connector and a first region provided with a plurality of through-holes, and a second plate, the second plate comprising a second connector configured for engaging the first connector and comprising a second region provided with a plurality of through-holes; wherein a porous membrane is interposed between the first region and the second region by engagement of the first connector and the second connector; (b) adding a biological sample to each of the through-holes of the first plate to form an immobilized sample on the porous membrane; and (c) measuring the target substance with a substance that specifically bonds with the target substance in the immobilized sample.

DETAILED DESCRIPTION

Figure 1:
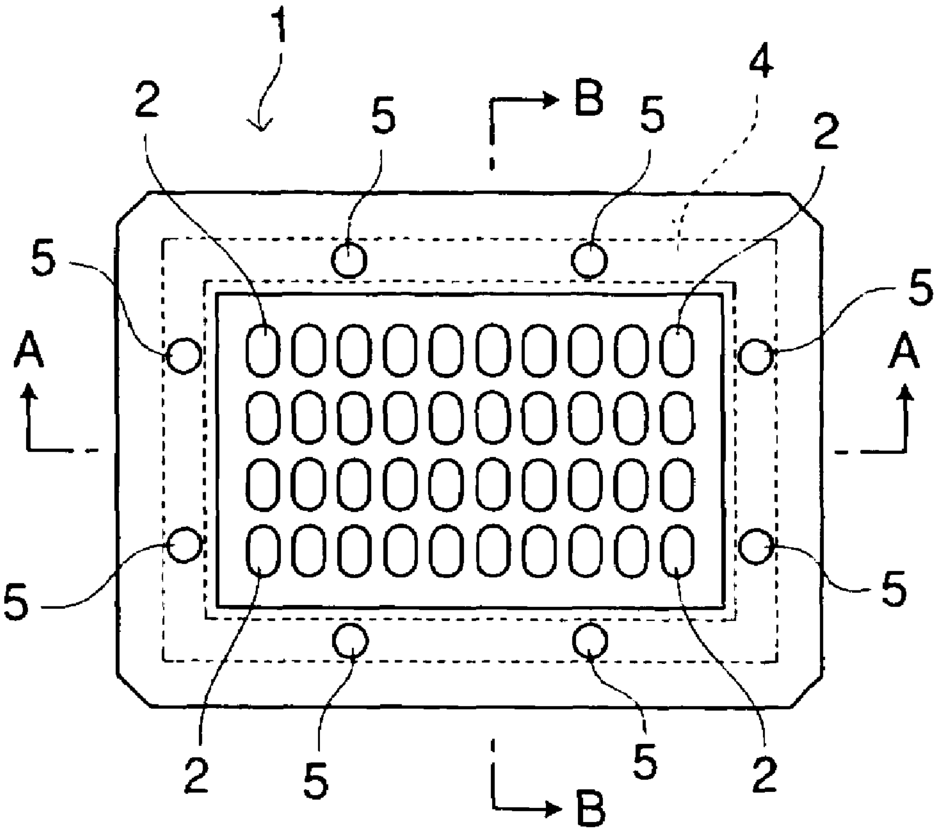
FIG. 1 is a top view of a top plate of an instrument for forming an immobilized sample on a porous membrane embodying features of the present invention.

In accordance with the present invention, instruments for forming an immobilized sample on a porous membrane have been discovered and are further described below. In addition, methods for the quantification of a target substance in an immobilized sample have been discovered, which are capable of quantifying a plurality of target substances and effectively quantifying the same target substance in a plurality of samples.

It is desirable that the instrument for forming an immobilized sample on a porous membrane have a structure including a first plate having a first connector and a first region provided with a plurality of through-holes; and a second plate having a second connector capable of engaging the first connector and a second region provided with a plurality of through-holes. At least a porous membrane is interposed between the first region and the second region by the engagement of the first connector and the second connector. According to this structure, a porous membrane is uniformly pressed between a first region and a second region, and excellent wells are formed by a plurality of through-holes.

It is desirable that the each of the plurality of through-holes is more ovoid than circular. Ovoid through-holes may be arrayed so as to have a higher density of holes as compared to circular through-holes.

The through-holes in the first plate have a top opening and a bottom opening. It is desirable that the top opening area is larger than the bottom opening area.

It is desirable that the through-holes are arranged in a matrix pattern. In this configuration, automated injection of the sample into the well formed by the through-hole may be readily accomplished.

It is desirable that the convexities and concavities have a close fitting tolerance of, for example, p6/H7, that allows disassembly. In this configuration, the convexities may be press-fitted to the concavities so as to be removable.

The hydrophobic porous membrane interposed between the first and second plates will be capable of hydrophobically binding with the protein, and specific examples of useful membranes include but are not limited to PVDF (polyvinylidene fluoride) hydrophobic membranes, nylon (subjected to an electrical charge process) membranes, nitrocellulose, and the like.

The average diameter of the pores of the hydrophobic membrane is between about 0.1 and about 10 μm, and preferably between about 0.1 and about 0.5 μm.

When forming an immobilized protein on the hydrophobic porous membrane, the protein does not pass through the hydrophobic porous membrane, even if the pores of the hydrophobic porous membrane are larger than the protein, since the protein is held by hydrophobic bonds and the like between the protein and the membrane.

It is desirable that the hydrophobic porous membrane is subjected to an initialization process, such as immersion in methanol or the like.

It is desirable that the first and second plates are formed of a chemically resistant material including but not limited to vinyl chloride resin and polyethylene resin.

In addition to the porous membrane, a filter may also be interposed between the first and second plates. The addition of a filter increases the water-tightness of the wells, and reduces fluid leakage from the wells. Furthermore, a filter may maintain moisture. Filter paper may be used as a filter. The thickness of the filter paper is desirably between about 0.2 and about 4 mm, and preferably between about 0.4 and about 2 mm. Furthermore, if the filter paper has a thickness within this range, one sheet may be used or a plurality of sheets may be used.

The present invention is further described below in reference to the examples shown in the drawings. It is to be understood that the present invention is not limited to these examples.

Instrument For Forming an Immobilized Sample on a Porous Membrane

Figure 2:
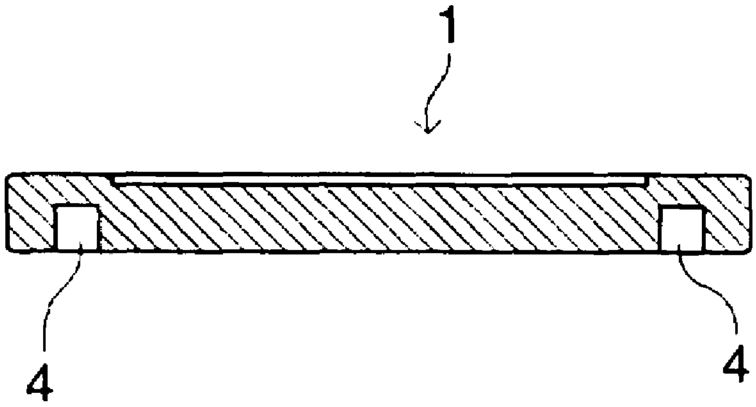
FIG. 2 is a cross-sectional view taken along the line A-A in FIG. 1.
Figure 3:
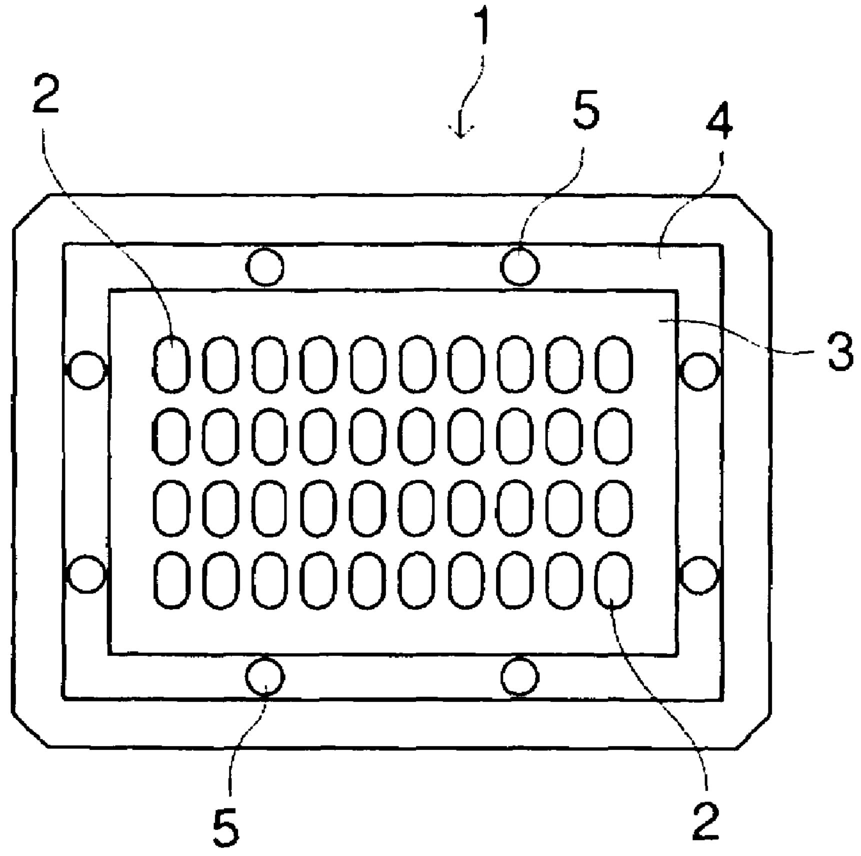
FIG. 3 is a bottom view of the top plate shown in FIG. 1.
Figure 4:
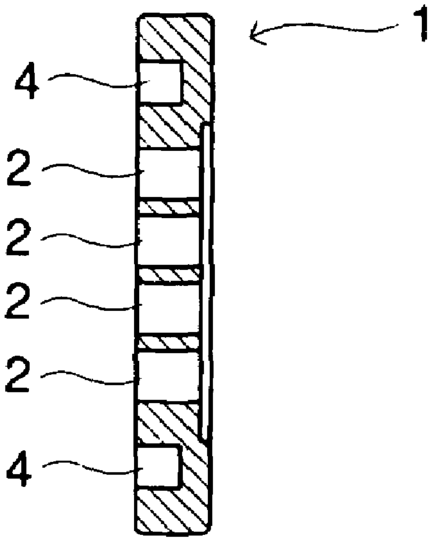
FIG. 4 is a cross-sectional view taken along the line B-B in FIG. 1.

FIG. 1 is a top view of the top plate of the instrument. FIG. 2 is a cross-sectional view taken along the line A-A in FIG. 1. FIG. 3 is a bottom view of the top plate. FIG. 4 is a cross-sectional view taken along the line B-B in FIG. 1.

As shown in these drawings, forty ovoid through-holes 2 arranged in a matrix-like pattern of 4 rows of ten holes each perforate a rectangular (70×50×7 mm) top plate 1. A single through-hole 2 has a cross section of approximately 13 $mm^2$. On the bottom surface of the top plate 1 is formed a channel (concavity) 4 having a width of 4 mm and a depth of 4 mm, which circumscribes the 40 through-holes 2. A rectangular porous membrane contact region 3 is isolated on the inner side by the channel 4. Furthermore, eight fixture through-holes 5 perforate the bottom of the channel 4.

Figure 5:
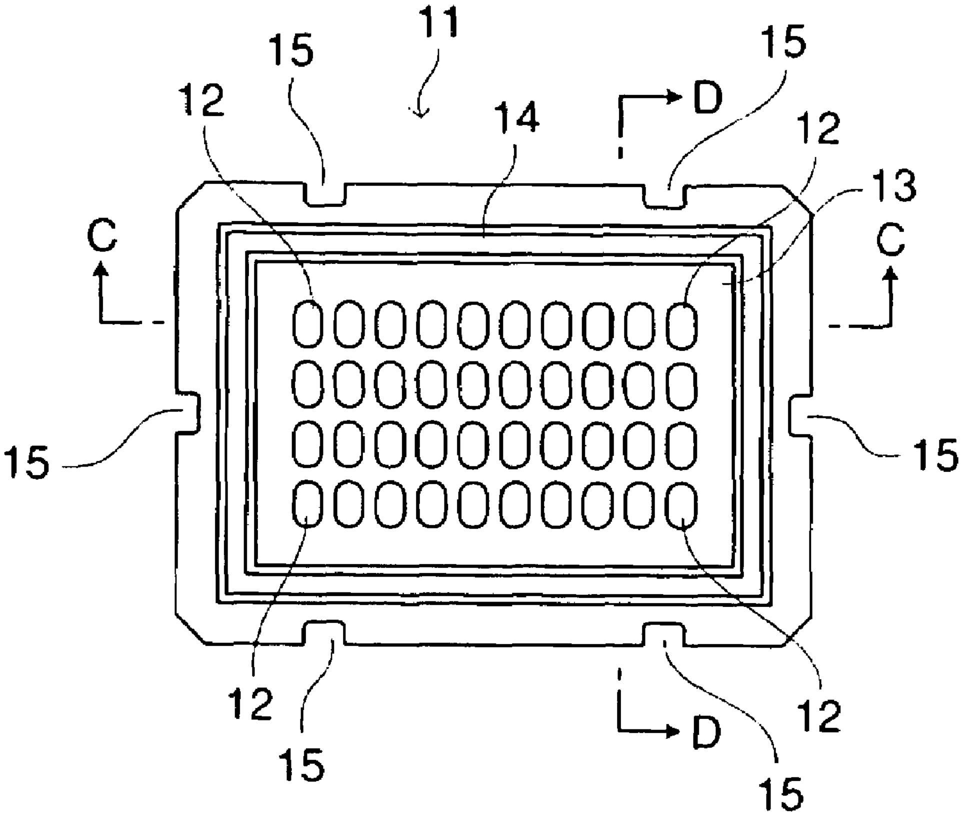
FIG. 5 is a top view of a bottom plate of an instrument embodying features of the present invention.
Figure 6:
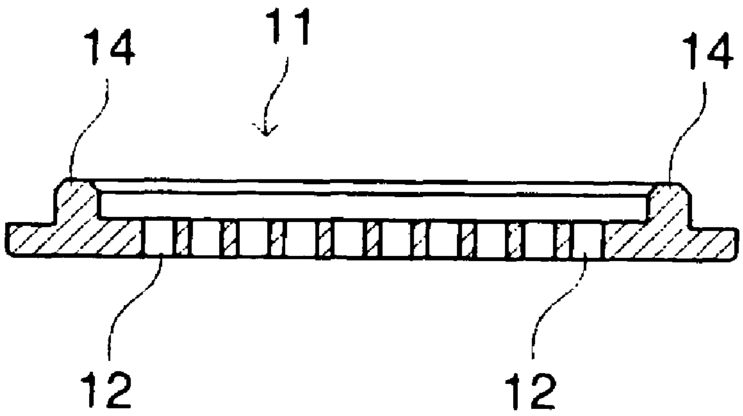
FIG. 6 is a cross-sectional view taken along the line C-C in FIG. 5.
Figure 7:
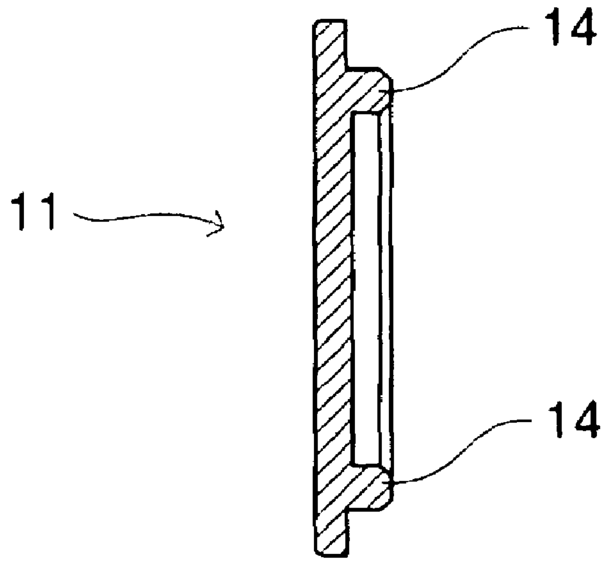
FIG. 7 is a cross-sectional view taken along the line D-D in FIG. 5.

FIG. 5 is a top view of a bottom plate of the instrument. FIG. 6 is a cross-sectional view taken along the line C-C in FIG. 5. FIG. 7 is a cross-sectional view on the line D-D in FIG. 5.

As shown in these drawings, on the rectangular (70×50×3 mm) bottom plate 11 are formed forty ovoid through-holes 12 arranged in a matrix of 4 rows of 10 holes each, which are respectively disposed at positions corresponding to the through-holes 2 of the top plate 1. The through-holes 12 have the same shape and cross section as the through-holes 2 (FIG. 1).

On the top surface of the bottom plate 11 is formed a rib-like convexity 14 having a height of 4 mm and a width of 4 mm circumscribing the forty through-holes 12 at a position which corresponds to the channel 4 (FIG. 1).

A rectangular porous membrane setting region 13 is isolated on the inner side by the convexity 14. Furthermore, six notches 15 are formed on the margin of the bottom plate 11. The top plate 1 and the bottom plate 11 are formed of vinyl chloride resin.

Figure 8:
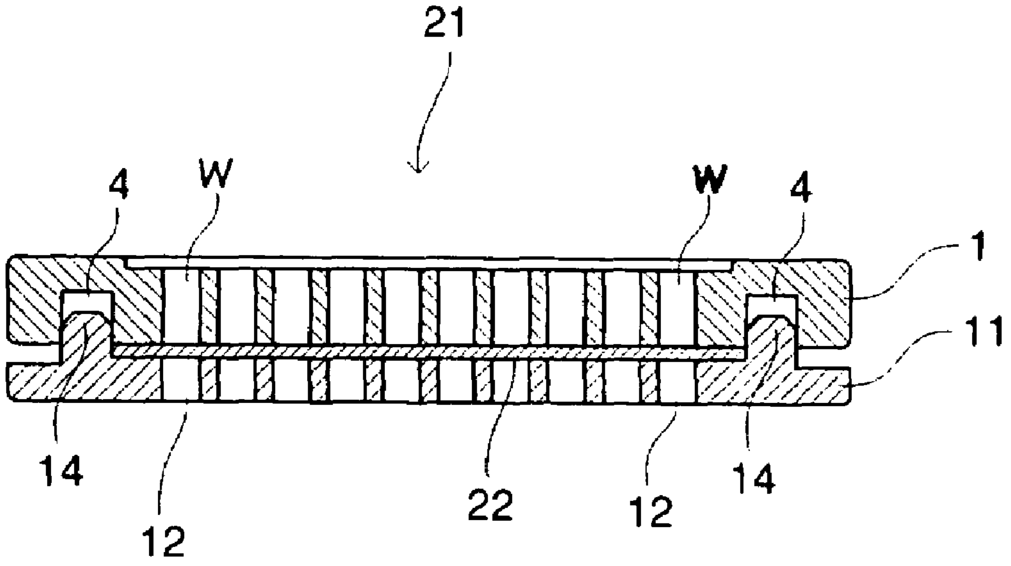
FIG. 8 is an assembly cross-sectional view of an instrument embodying features of the present invention.

FIG. 8 is a cross-sectional view of an instrument 21. The top plate 1 and the bottom plate 11 are overlaid, and the convexity 14 is press-fitted onto the channel 4 so as to be removable. In this configuration, the through-holes 2 and the through-holes 12 mutually have the same axis. The inner surface of the convexity 14 and the corresponding contact surface of the channel 4 have a fit tolerance of p6/H7.

During use, a rectangular, hydrophobic, and porous membrane 22 is installed between the porous membrane setting regions 3 and 13, and subjected to uniform compression by press-fitting the convexity 14 into the channel 4. In this configuration, the porous membrane 22 is watertight and isolated by the through-holes 2, and a number of wells (sumps) W are formed in correspondence to the number of through-holes 2.

Figure 23:
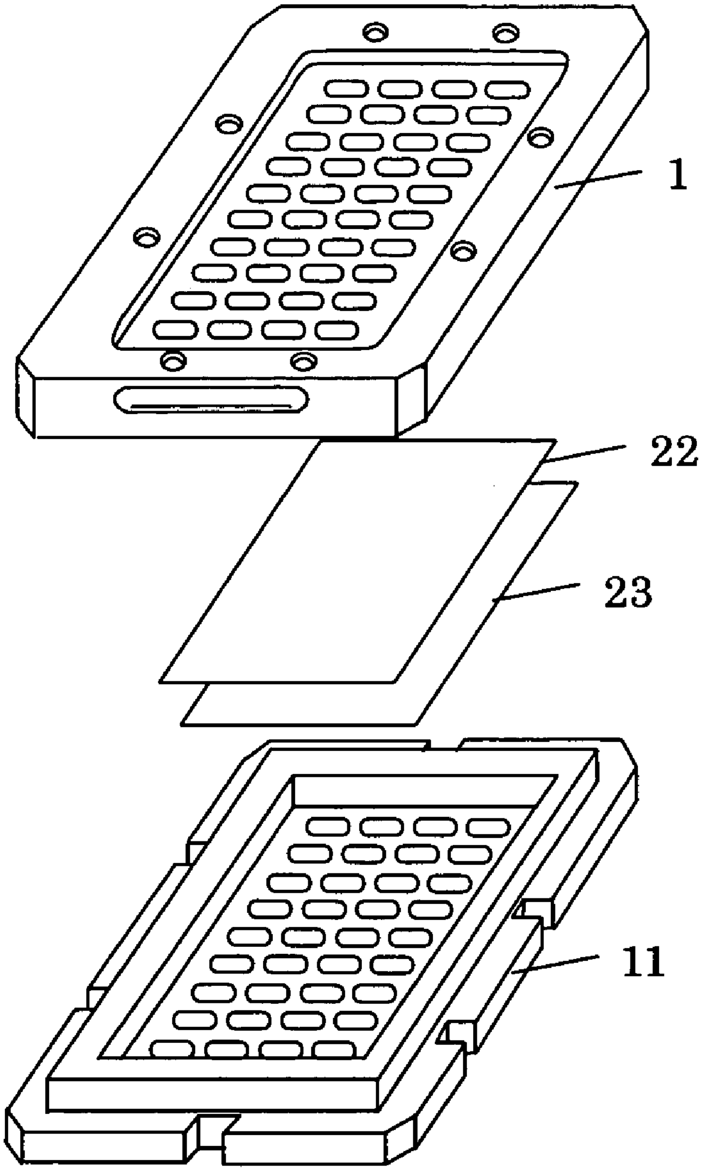
FIG. 23 is a perspective view showing the structure of an instrument embodying features of the present invention.

FIG. 23 is a perspective view showing the structure of the instrument. The structure shows a porous membrane 22 and a filter paper 23 interposed between the top plate 1 and the bottom plate 11. The watertight isolation of the porous membrane 22 in each through-hole 2 is greater when a filter paper 23 is also interposed than when the porous membrane 22 alone is used, thereby reducing the fluid leakage from the through-holes 2.

Immobilized Sample Preparing Apparatus

Figure 9:
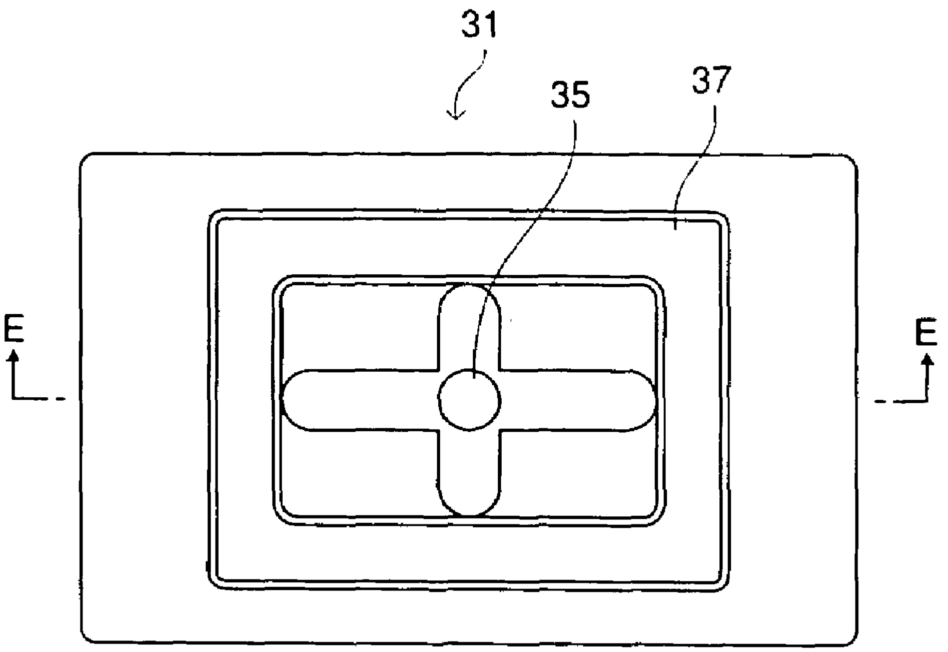
FIG. 9 is a top view of a sample preparation apparatus.
Figure 10:
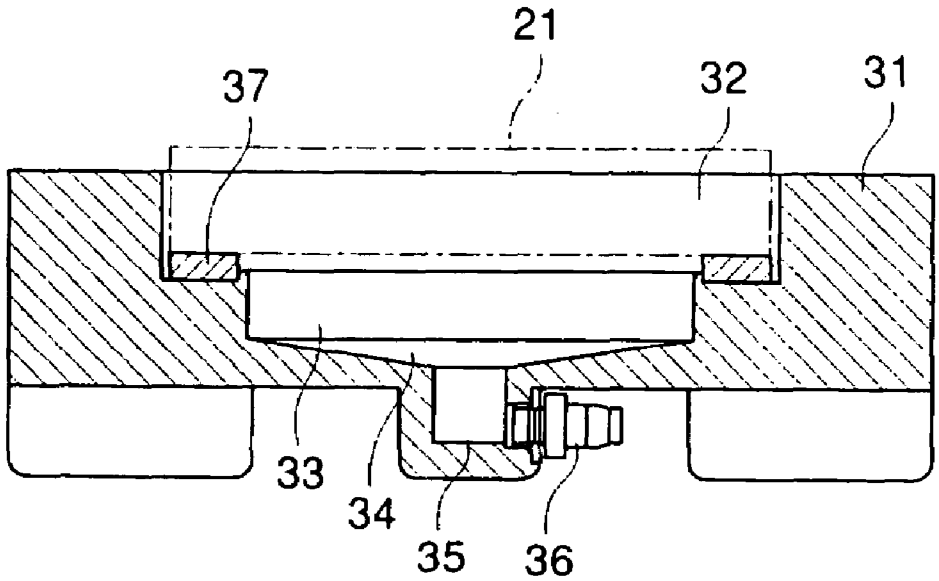
FIG. 10 is a cross-sectional view taken along the line E-E in FIG. 9.

FIG. 9 is a top view of the immobilized sample preparation apparatus. FIG. 10 is a cross-sectional view taken along the line E-E arrow in FIG. 9.

As shown in these drawings, the apparatus body 31 is formed of an aluminum block, the top surface of which is provided with a rectangular first concavity 32, and a rectangular second concavity 33 on the bottom of the first concavity 32. A rectangular frame-like flexible rubber gasket 37 is provided on the margin of the second concavity 33 on the bottom surface of the first concavity 32.

The bottom surface of the second concavity 33 is provided with a cross-shaped channel 34, and the center of the bottom is provided with a suction port 35. The bottom of the channel 34 is inclined so as to deepen from the margin of the second concavity toward the center. The suction port 35 is connected to a nipple 36 provided for connecting to an external suction pump (not shown).

An instrument 21 assembled as shown in FIG. 8 is installed horizontally through the bottom surface gasket 37 of the concavity 32 of the body 31 of the immobilized sample preparation apparatus. After injecting or dripping a sample fluid containing a protein into each well W of the protein instrument 21, a suction pump (not shown) which is connected to the nipple 36 is operated.

In this manner, the instrument 21 is attached air-tightly to the bottom surface of the concavity 32 through the gasket 37, and the sample fluid within each well W is suctioned through the porous membrane 22, such that the protein to be measured forms an immobilized sample on the membrane 22. In this case, an anchoring member may also be provided on the body 31 so as to press against and anchor the instrument 21 to the bottom surface of the concavity 32.

Then, a labeled antibody is injected into each well W. After binding with a specific protein, a washing process is performed. In this manner, the immunocomplex of the detection target protein and the labeled antibody is prepared on the porous membrane 22. Then, the instrument 21 is disassembled and the porous membrane 22 is removed. The immobilized sample on the porous membrane 22 is optically measured and the amount of the target protein is calculated.

Instrument Assembly Apparatus

Figure 11:
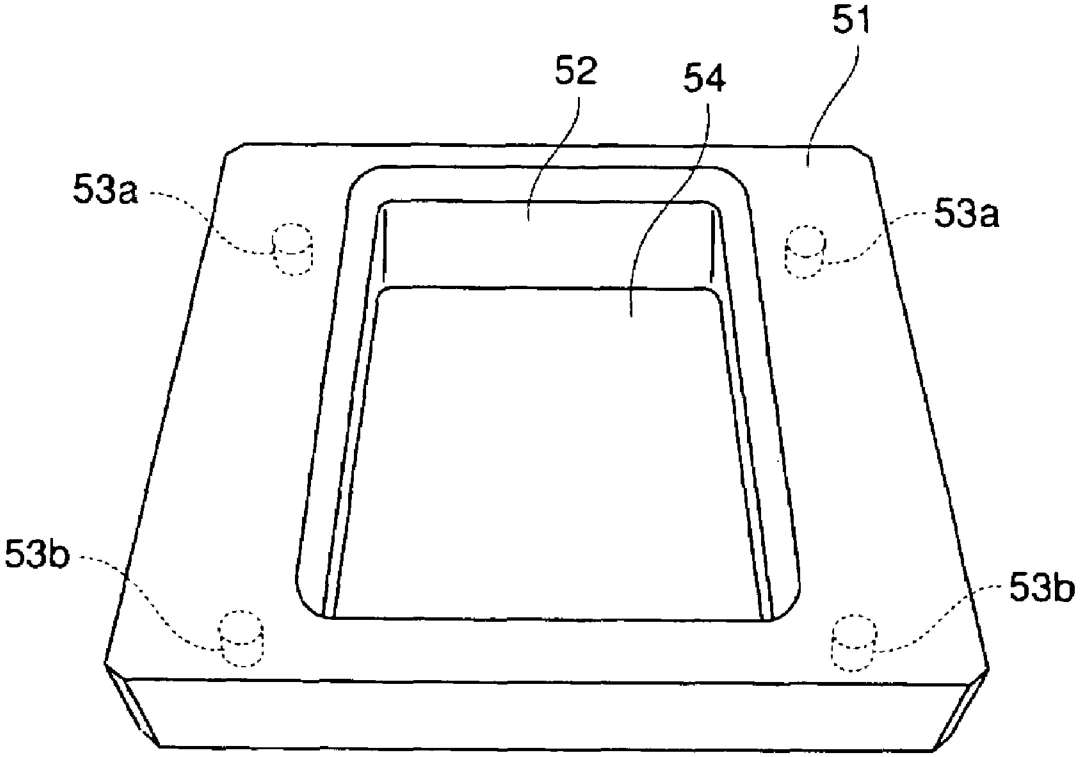
FIG. 11 is a perspective view of an instrument assembly apparatus embodying features of the present invention.
Figure 12:
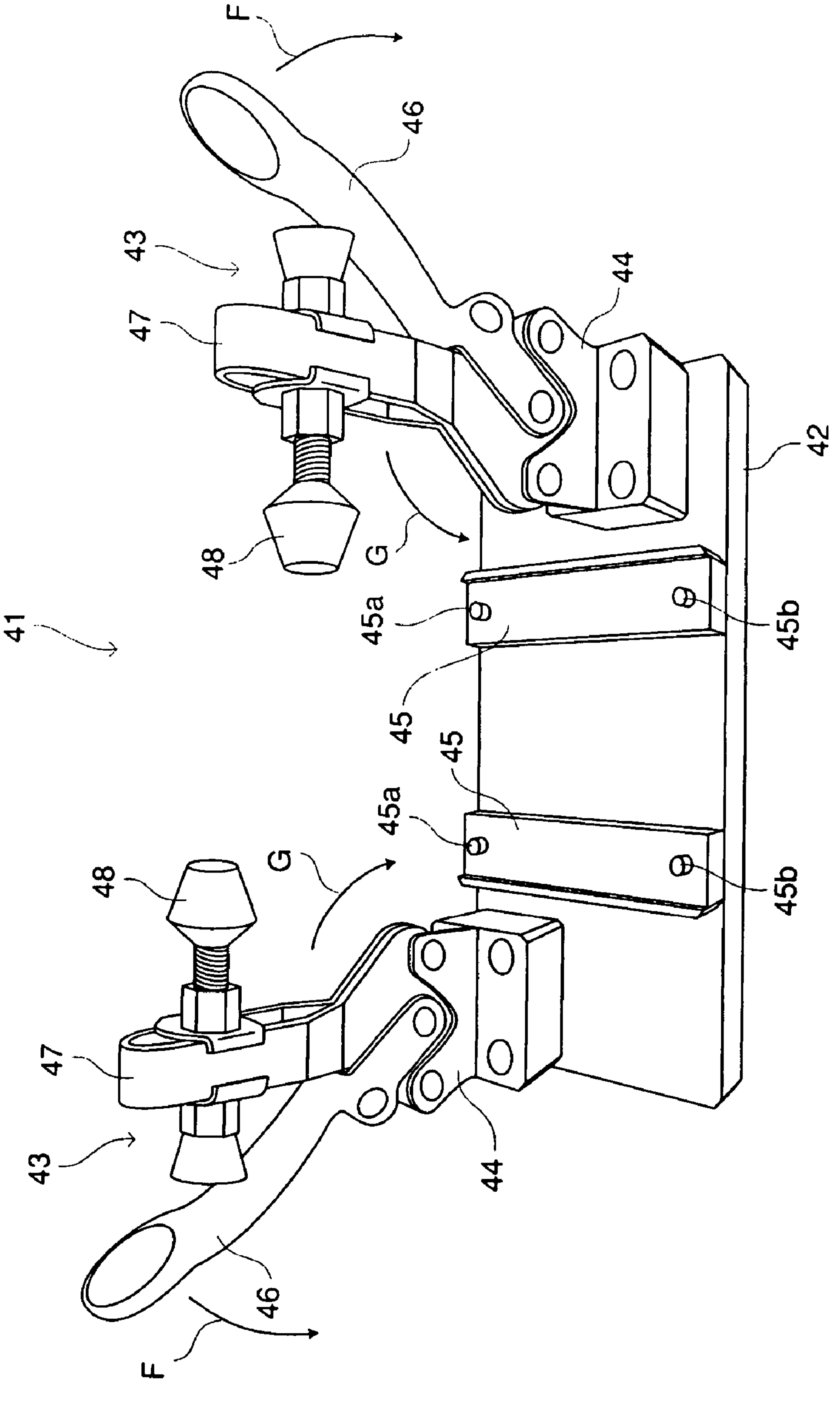
FIG. 12 is a perspective view of an instrument assembly and disassembly apparatus embodying features of the present invention.

FIGS. 11 and 12 are perspective views of the assembly part 51 and the pressure part 41, respectively, forming the instrument assembly apparatus. As shown in FIG. 11, the assembly part 51 has a rectangular concavity 52 for accommodating and assembling the top plate 1 (FIG. 1) and the bottom plate 11 (FIG. 5) on the surface of a flat plate of aluminum. The concavity 52 is provided with a flat bottom 54. The back surface of the assembly part 51 is provided with two sets of positioning concavities 53*a* and 53*b*.

As shown in FIG. 12, the pressure part 41 is provided with two pressure clamps 43 which are symmetrically arranged, and two guide plates 45 horizontally arranged on a stationary plate 42. Positioning pins 45*a* and 45*b* respectively project at right angles from the two guide plates 45. In the present example, a commercial model HH450 (Misumi Corporation) is used for the pressure clamp 43. The pressure clamp 43 is provided with a toggle mechanism 44, such that an arm 47 is rotated in the direction of arrow G by pressing a handle 46 in the direction of arrow F so as to hold a rubber head 48 in a predetermined position.

The sequence for assembling the instrument 21 shown in FIG. 8 is described below in terms of this structure.

Figure 13:
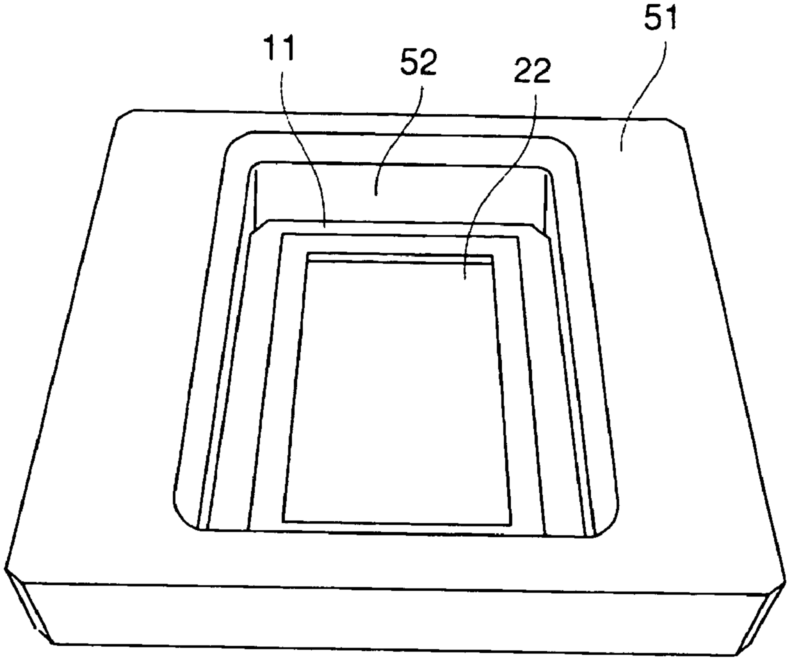
FIG. 13 is a first illustration showing an instrument assembly sequence.

First, after a desired hydrophobic porous membrane 22 (FIG. 8) is placed in the porous membrane setting region 13 of the bottom plate 11 (FIG. 5), the bottom plate 11 is inserted into the concavity 52 of the assembly part 51 and placed so as to be horizontal on the bottom 54, as shown in FIG. 13.

Figure 14:
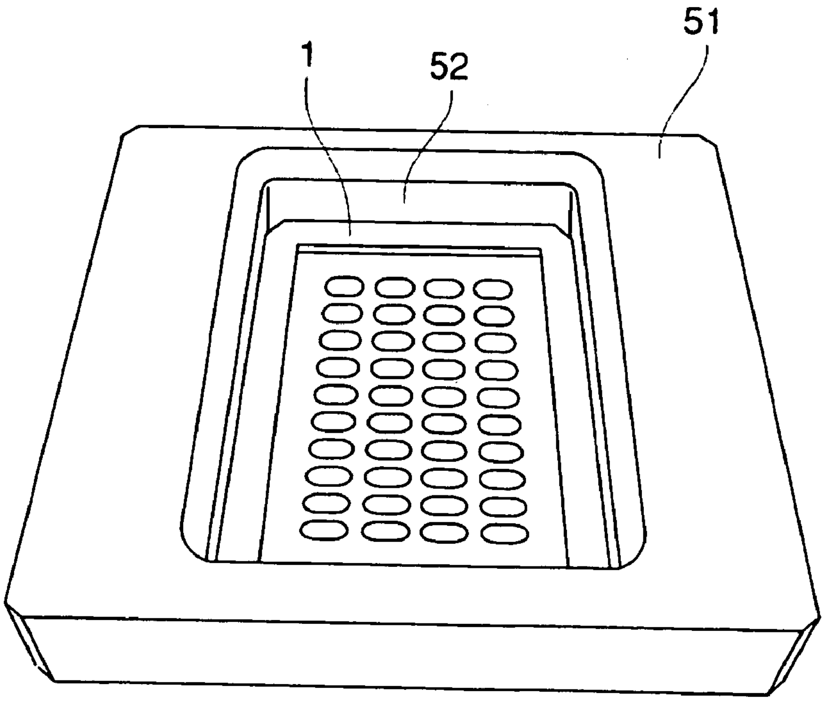
FIG. 14 is a second illustration showing an instrument assembly sequence.
Figure 15:
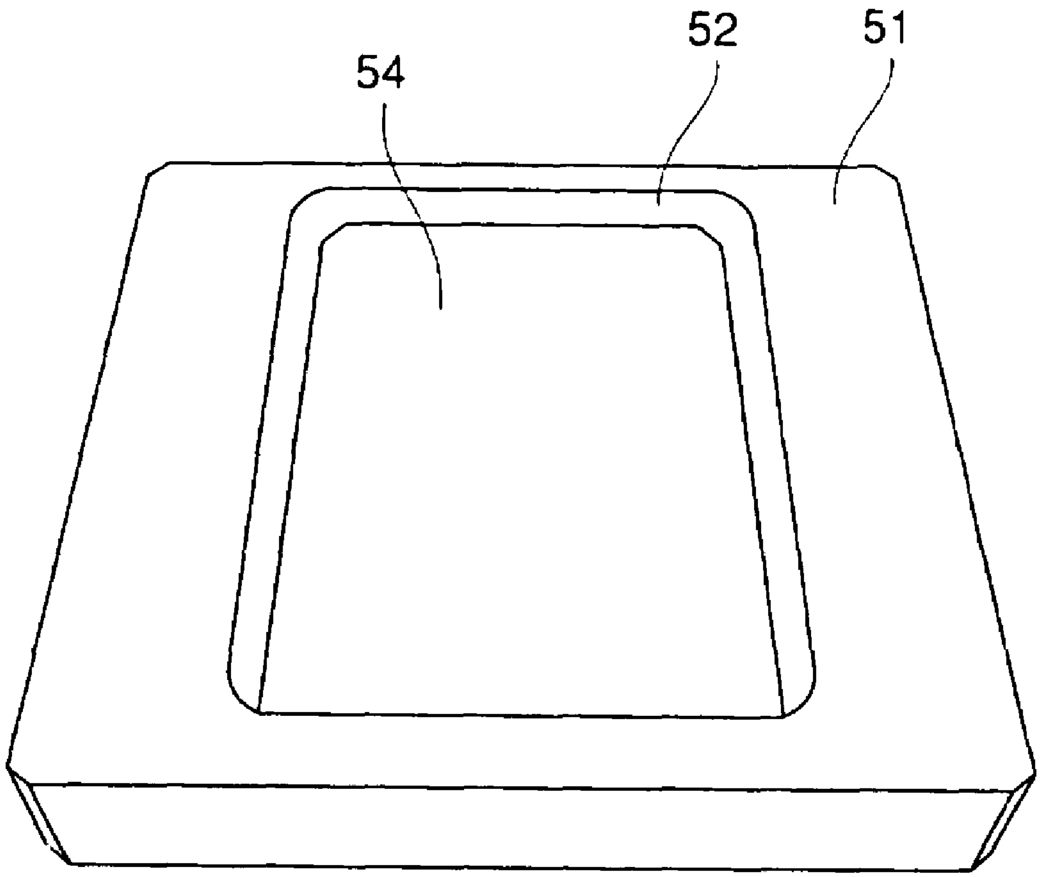
FIG. 15 is a third illustration showing an instrument assembly sequence.

Next, the top plate 1 (FIG. 1) is inserted horizontally, on the concavity 52 with the channel 4 face down, so as to overlay the bottom plate 11, as shown in FIG. 14. Then, the rectangular flat plate 54 is inserted in the concavity 52 so as to be on top of the top plate 1, as shown in FIG. 15.

Then, the assembly part 51 is placed on top of the two guide plates 45 of the pressure part 41 shown in FIG. 12. This time, the two sets of positioning pins 45*a* and 45*b* are respectively inserted into the two sets of concavities 53*a* and 53*b* on the back surface of the assembly part 51.

Figure 16:
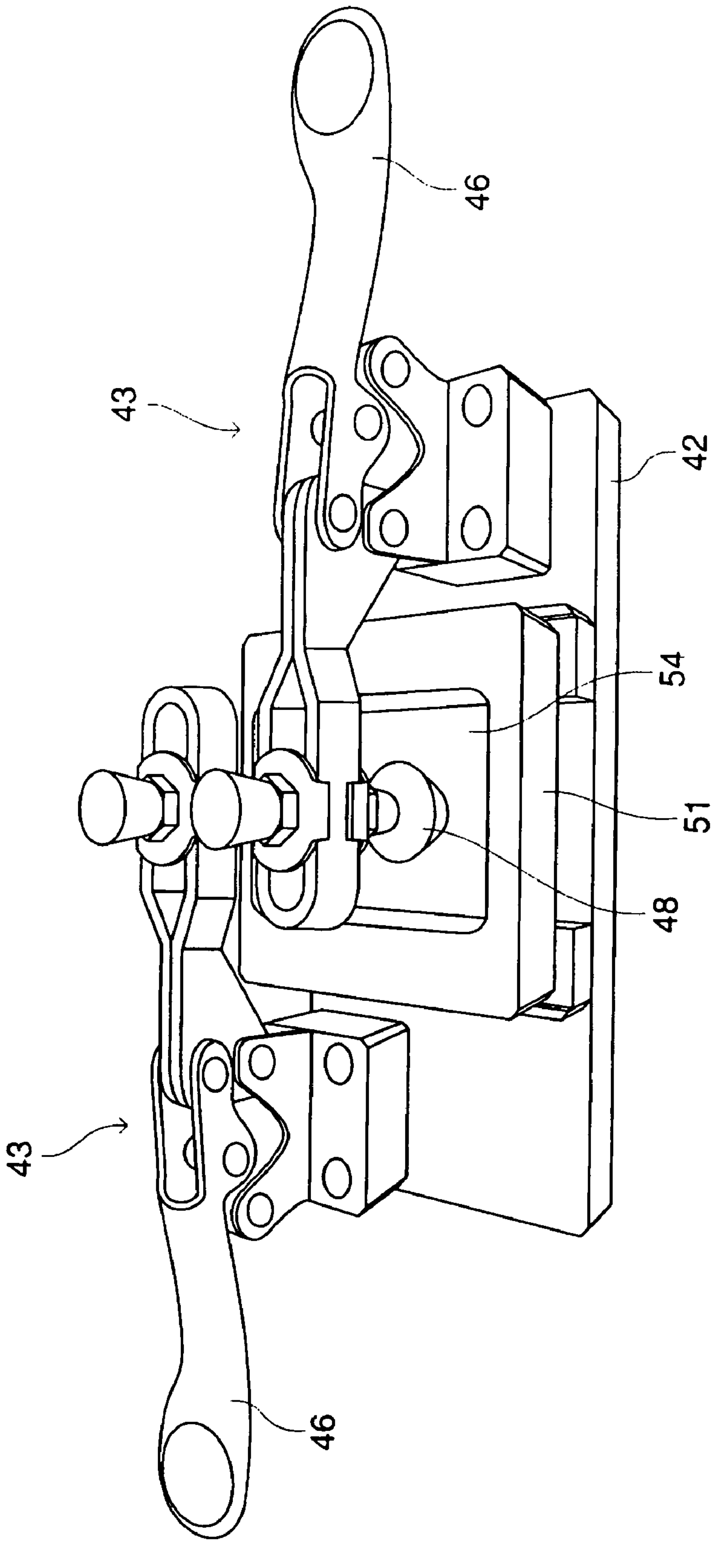
FIG. 16 is a fourth illustration showing an instrument assembly sequence.

Then, when each handle 46 of the two pressure clamps 43 is pressed in the direction of arrow F, each head 48 is rotated in the direction of arrow G, and the plate 54 is pressed and held in a pressured state, as shown in FIG. 16. In this manner, the convexity 14 of the bottom plate 11 is press-fitted onto the channel 4 of the top plate 1. In conjunction with this action, the porous membrane 22 is held under uniform pressure between the top plate 1 and the bottom plate 11. In this manner, the instrument 21 shown in FIG. 8 is completed.

Instrument Disassembly Apparatus

Figure 17:
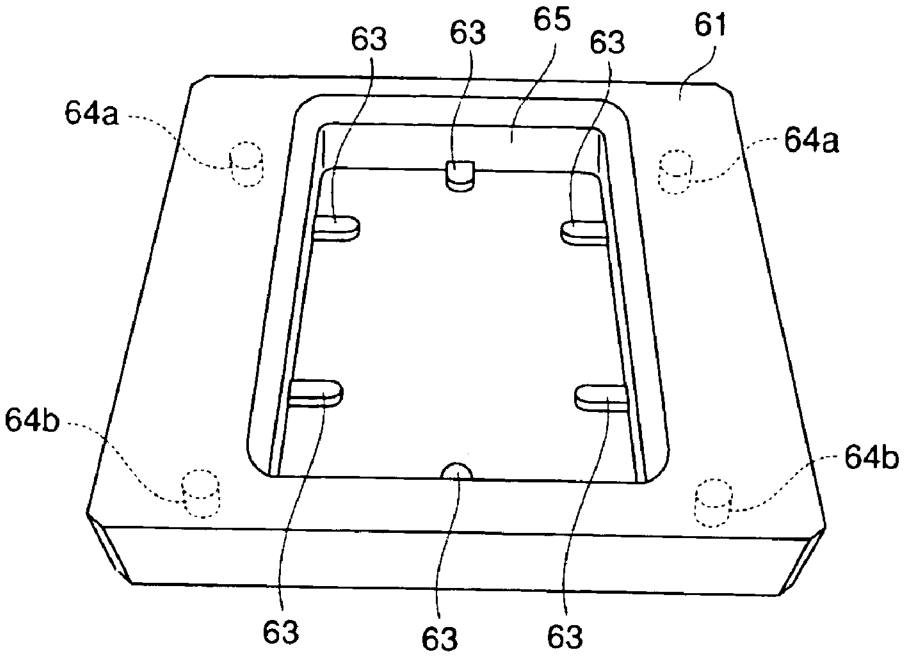
FIG. 17 is a perspective view of an instrument disassembly apparatus embodying features of the present invention.
Figure 18:
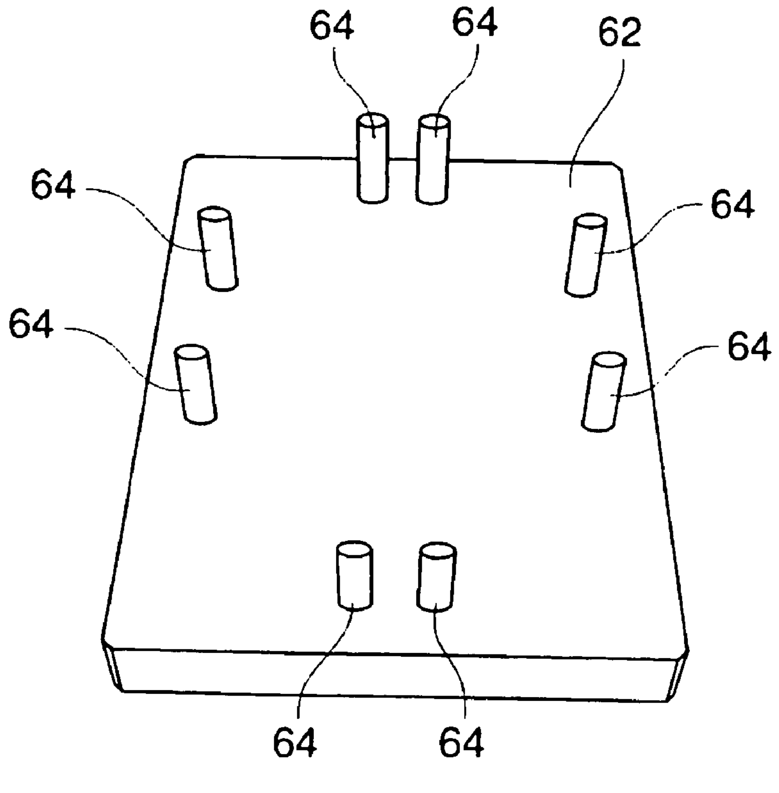
FIG. 18 is a perspective view of an instrument disassembly apparatus embodying features of the present invention.

FIGS. 17 and 18 are perspective views showing the instrument support part 61 and press plate 62, which form the instrument disassembly apparatus.

As shown in FIG. 17, the instrument support part 61 has a rectangular open window 65, and the back surface is provided with two sets of positioning concavities 64*a* and 64*b*. The open window 65 is provided with six stoppers 63 which protrude horizontally from the inner wall. Furthermore, the press plate 62 is provided with eight extraction pins 64 rising perpendicular to the surface.

The sequence of disassembling the instrument in this structure is described below. The press plate 62 is placed on top of the instrument 21 and the extraction pins 64 of the press plate 62 are respectively inserted into the six fixture through-holes 5 of the top plate 1 of the assembled instrument 21 shown in FIG. 8, such that the instrument 21 is held by the press plate 62.

Figure 19:
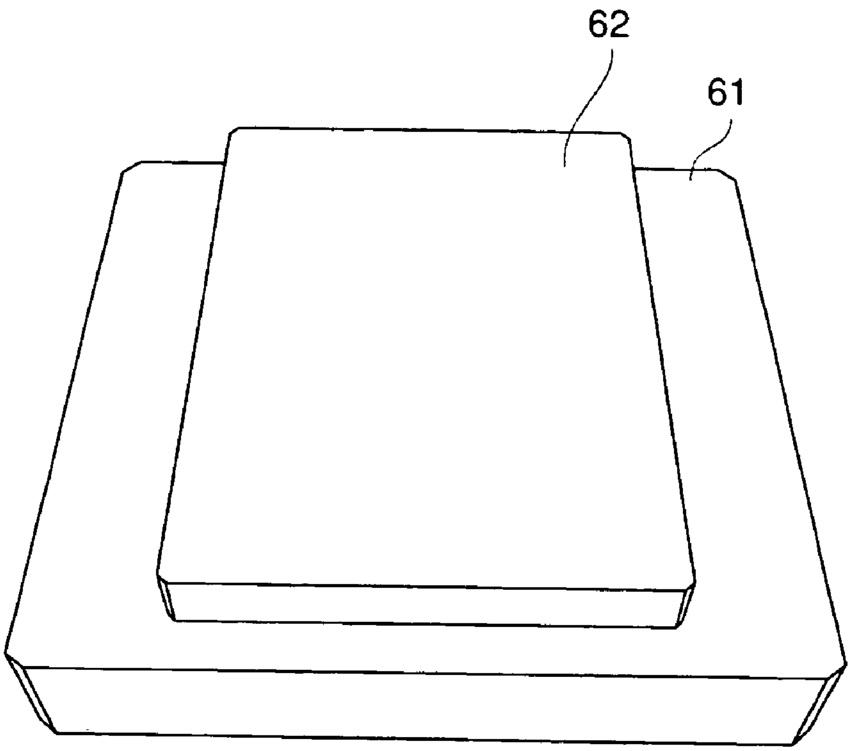
FIG. 19 illustrates the operation of an instrument disassembly apparatus embodying features of the present invention.

The press plate 62 is inserted horizontally below the instrument 21, as shown in FIG. 19, toward the open window 65 of the instrument support part 61. This time, the six stoppers 63 pass through the notches 15 of the bottom plate 11, and engage the margin of the bottom surface of the top plate 1.

Next, the instrument support part 61 is inserted on the two guide plates 45 of the pressure part 41 shown in FIG. 12. This time, the two sets of positioning pins 45*a* and 45*b* are respectively inserted into the two sets of concavities 64*a* and 64*b* on the back surface of the instrument support part 61.

Then, when each of the handles of the two pressure clamps 43 shown in FIG. 12 is pressed in the direction of arrow F, each head 48 is rotated in the direction of arrow G and presses the press plate 62. This pressure state is maintained. At the same time, the convexity 14 of the bottom plate 11 is extracted from the channel 4 of the top plate 1 by the eight extraction pins 64. In this manner, the bottom plate 11 is separated from the top plate 1, and drops downward. Then, the porous membrane 22 is removed from the dropped bottom plate 11.

Protein Measurement

An example of protein measurement is described below.

In the present measurement example, quantification of the amounts of CDK1 (Cyclin dependent protein kinase 1) respectively contained in ten samples is performed using a single instrument 21 (FIG. 8).

CDK1 is an enzyme protein which controls the progress of the cell cycle. In addition to CDK1, other enzyme proteins which control the progress of the cell cycle include CDK1, CDK4, CDK6, CyclineB, CyclineD, CyclineE, P16, P21, P27, C-myc, and the like.

(a) Reagent Preparation

First, the reagent and samples are prepared in the manner described below.

(1) Loading Buffer

TBS (tris buffer saline)

(Constituents: 25 mM tris (pH7.4) and 150 mM sodium chloride aqueous solution)

(2) Standard Reagent

Recombinant CDK1 antibody was diluted with a TBS solution containing 0.005% NP-40 (surface-active agent) and 2.5 μg/50 μL BSA, so as to prepare reagents having five levels of CDK1 antibody concentration: 50 ng/mL, 125 ng/mL, 250 ng/mL, 390 ng/mL, and 500 ng/mL.

(3) Specimens (10 Specimens)

After specimens collected from cells and tissue were homogenized, a product in the form of a crude protein solution from which insoluble matter had been removed was diluted with TBS solution containing less than 0.005% NP-40 (surface-active agent) to obtain a total protein amount of 2.5 μg/50 μL.

(4) Control Sample (Two Samples)

Control samples were prepared using HL60 and Jurkat. They were cultured cells of leukemic origin and diluted with TBS solution containing less than 0.005% NP-40 (surface-active agent) to obtain a total protein amount of 2.5 μg/50 μL.

(5) Background Solution

The background solution had a CDK1 concentration of 0.0 μg/50 μL (less than 0.005% NP-40 (surface-active agent) diluted with TBS solution containing 2.5 μg/50 μL BSA (bovine serum albumin)).

(6) Wash

TBS (tris buffer saline) (constituents: 25 mM tris (pH7.4) and 150 mM sodium chloride aqueous solution).

(7) Blocking Reagent

The blocking agent was TBS solution with 4% BSA (bovine serum albumin).

(8) Primary Antibody Reagent

The primary antibody reagent was 4 μg/mL rabbit antibody-CDK1 antibody diluted with 80% blocking agent (Block Ace; Dainippon Pharmaceutical Co., Ltd.).

(9) Secondary Antibody Reagent

The secondary antibody reagent was 4 μg/mL biotin antibody-rabbit antibody adjusted with TBS and 1% BSA.

(10) FITC-Labeled Reagent

The FITC-labeled reagent was 10 μg/mL FITC (fluoresceinisothiocyanate)-labeled streptavidin diluted with TBS and 1% BSA.

(11) Rinsing Reagent

The rinsing reagent was 20% methanol.

(b) Measurement Sequence

Measurement was performed in the following sequence.

[1] A single layer PVDF membrane was prepared as the hydrophobic porous membrane 22, and immersed in methanol.

[2] The membrane was then immersed in the loading buffer of section (1).

[3] The membrane of section [1] was set in the bottom plate 11, then placed on the top plate 1.

[4] Using the instrument assembly apparatus, the instrument 21 holding membrane was assembled.

Figure 20:
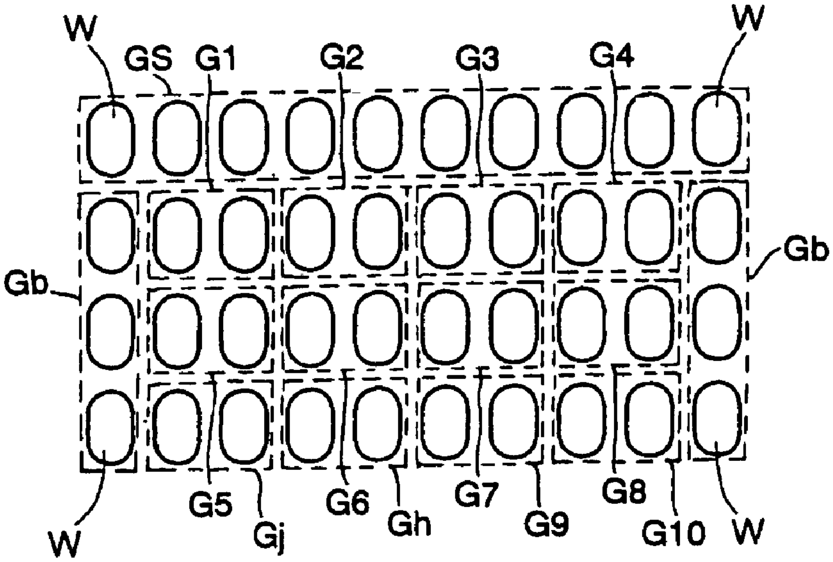
FIG. 20 illustrates the group divisions of wells of an instrument embodying features of the present invention in a protein measurement example.

[5] The instrument 21 was set in the immobilized sample preparation apparatus (FIG. 9). The forty wells W of the instrument 21 were grouped beforehand into standard series group Gs, background group Gb, control specimen groups Gj and Gh, and specimen groups G1 through G10, as shown in FIG. 20.

[6] Each of the standard reagents of section (2) having five levels of concentration was injected at a rate of 50 μL per well into each two wells W of the standard group Gs.

[7] Each of the ten types of specimens of section (3) was injected at a rate of 50 μL per well into each two wells of the groups G1 through G10.

[8] The two types of control specimens of section (4) were injected at a rate of 50 μL per well into each two wells W of the groups Gj and Gh.

[9] The background solution of section (5) was injected at a rate of 50 μL per well into each well of the group Gb.

[10] After the injections were completed, the samples were suctioned from the suction port 35 at a negative pressure of 150 mmHg for approximately 30 seconds to prepare an immobilized sample pattern on the membrane.

[11] The wash solution of section (6) was injected at a rate of 50 μL per well into all wells W of the instrument 21, and suctioning under negative pressure of 500 mmHg was performed for approximately 15 seconds to accomplish washing.

[12] The blocking solution of section (7) was injected at a rate of 50 μL per well into all wells W of the instrument 21 and allowed to stand for approximately 15 minutes.

[13] Suctioning was performed for approximately 15 seconds under a negative pressure of 500 mmHg.

[14] The primary antibody sample of section (8) was injected at a rate of 50 μL per well into all wells W of the instrument 21 and allowed to stand for approximately 30 minutes.

[15] Suctioning was performed for approximately 15 seconds under a negative pressure of 500 mmHg.

[16] The wash solution of section (6) was injected at a rate of 50 μL per well into all wells W of the instrument 21, and suctioning under negative pressure of 500 mmHg was performed for approximately 15 seconds to accomplish washing. This procedure was repeated five times.

[17] The secondary antibody sample of section (9) was injected at a rate of 50 μL per well into all wells W of the instrument 21 and allowed to stand for approximately 30 minutes.

[18] Suctioning was performed for approximately 15 seconds under a negative pressure of 500 mmHg.

[19] The wash solution of section (6) was injected at a rate of 50 μL per well into all wells W of the instrument 21, and suctioning under negative pressure of 500 mmHg was performed for approximately 15 seconds to accomplish washing. This procedure was repeated three times.

[20] The FITC-labeled reagent of section (10) was injected at a rate of 50 μL per well into all wells W of the instrument 21 and allowed to stand for approximately 30 minutes.

[21] Suctioning was performed for approximately 15 seconds under a negative pressure of 500 mmHg.

[22] The wash solution of section (6) was injected at a rate of 50 μL per well into all wells W of the instrument 21, and suctioning under negative pressure of 500 mmHg was performed for approximately 15 seconds to accomplish washing. This procedure was repeated five times.

[23] The instrument 21 was removed from the apparatus 31.

[24] The instrument 21 was disassembled by the instrument disassembly apparatus, and the membrane was removed.

[25] The removed membrane was lightly rinsed with the rinsing reagent of section (11).

[26] The membrane was dried at room temperature for 20 minutes.

[27] The fluorescent intensity was measured using a fluorescence reading device.

(c) Results

When the average fluorescent intensity of the immobilized background solution in group Gb of FIG. 20 is designated as the corrected background fluorescent intensity Ib, and a value 4 times the standard deviation is designated as the measurement lower limit of detection Imin, the following may be derived from actual measurements.

Ib=176.3 (count/$mm^2$)

Imin=35.4 (count/$mm^2$)

Figures 21, 22:
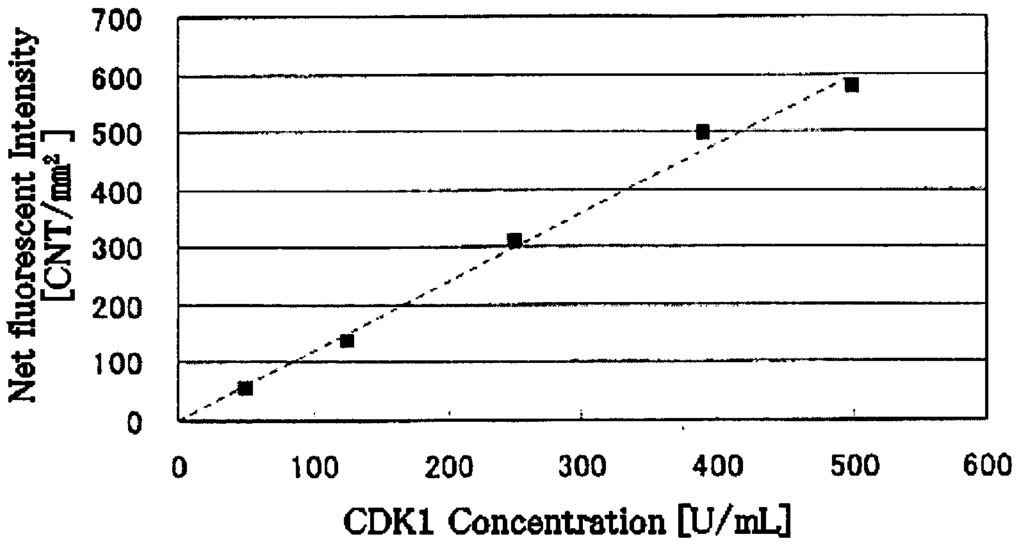
FIG. 21 shows a protein measurement result.
FIG. 22 shows a calibration curve in the protein measurements.

The calibration curve shown in FIG. 22 is prepared by subtracting Ib from the fluorescent intensity Is of the immobilized standard reagent in the standard series group Gs, and by calculating the net fluorescent intensity Iso. One ng/50 μL of the standard reagent of section (2) allows recognition of 1 U/50 μL of CDK1 in the sample.

In regard to the ten specimens and two control specimens, the average fluorescent intensity was calculated for each two wells, respectively. Ib was subtracted and the net fluorescent intensity was calculated. The CDK1 concentration in each specimen was calculated using the calibration curve of FIG. 22 from the calculation results. These calculation results are shown in FIG. 21.

In FIG. 21, specimens having a net fluorescent intensity less than Imin are designated by ND (not measurable). In the control specimens, HL60 is known to be 150 to 250 count/$mm^2$, and Jurkat is known to be 380 to 550 count/$mm^2$. Since the values of HL60 and Jurkat are within this range in FIG. 21, these measurements are judged to be correct.

The foregoing detailed description has been provided by way of explanation and illustration, and is not intended to limit the scope of the appended claims. Many variations in the presently preferred embodiments illustrated herein will be obvious to one of ordinary skill in the art, and remain within the scope of the appended claims and their equivalents.

What is claimed is:

1. An instrument for forming an immobilized sample on a porous membrane comprising:

a first plate comprising a first connector and a first region provided with a plurality of through-holes;

a second plate comprising a second connector configured for engaging the first connector and a second region provided with a plurality of through-holes; and a porous membrane interposed between the first region and the second region by engagement of the first connector and the second connector;

wherein the second connector comprises a rib-like convexity circumscribing the second region, and wherein the first connector comprises a concavity configured to engage the convexity.

2. The instrument of claim 1, wherein each of the through-holes provided in the first region confronts a corresponding through-hole provided in the second region when the first connector is engaged with the second connector.

3. The instrument of claim 2, wherein each of the through-holes provided in the first region shares an axis with each of the through-holes provided in the second region.

4. The instrument of claim 1, wherein the porous membrane and the through-holes provided in the first region form wells when the first connector is engaged with the second connector.

5. The instrument of claim 4, wherein the wells corresponding to each of the through-holes provided in the first region are formed so as to be substantially watertight.

6. The instrument of claim 1, wherein each of the through-holes formed in the first region and each of the through-holes formed in the second region are substantially ovoid in shape.

7. The instrument of claim 1, wherein the through-holes provided in the first region are arranged in a matrix pattern in the first region, and wherein the through-holes provided in the second region are arranged in a matrix pattern in the second region.

8. The instrument of claim 1, wherein the concavity and the convexity have a close fitting tolerance.

9. The instrument of claim 8, wherein the close fitting tolerance is p6/H7.

10. The instrument of claim 1, further comprising a filter, wherein the filter is interposed between the first region and the second region by engagement of the first connector and the second connector.

11. The instrument of claim 10, wherein the filter comprises filter paper.

12. The instrument of claim 1, wherein the immobilized sample comprises an immobilized protein.

13. The instrument of claim 1, wherein the first connector is arranged outside of the first region.

14. The instrument of claim 1, wherein the interposed porous membrane comprises a first surface contacting the first region and a second surface contacting the second region.

15. The instrument of claim 1, wherein the concavity is press-fitted onto the convexity.

16. The instrument of claim 1, wherein the second region comprises a flat surface.

17. The instrument of claim 1, wherein the porous membrane is hydrophobic.

* * * * *